United States Patent [19]

Kirsten et al.

[11] Patent Number: 5,236,923
[45] Date of Patent: Aug. 17, 1993

[54] SUBSTITUTED PYRIMIDYLAMIDE OXIMES

[75] Inventors: Rolf Kirsten, Monheim; Hilmar Wolf, Langenfeld; Gerd Hänssler, Leverkusen; Heinz-Wilhelm Dehne, Monheim; Stefan Dutzmann, Hilden, all of Fed. Rep. of Germany

[73] Assignee: Bayer Aktiengesellschaft, Leverkusen, Fed. Rep. of Germany

[21] Appl. No.: 798,685

[22] Filed: Nov. 26, 1991

[30] Foreign Application Priority Data

Dec. 12, 1990 [DE] Fed. Rep. of Germany ....... 4039630

[51] Int. Cl.$^5$ ................... A01N 43/54; C07D 239/26; C07D 239/34; C07D 239/42
[52] U.S. Cl. .................... 514/256; 514/241; 514/258; 514/259; 514/269; 544/217; 544/218; 544/219; 544/180; 544/296; 544/253; 544/319; 544/326; 544/327; 544/328; 544/329; 544/333; 544/334; 544/335; 544/298
[58] Field of Search ............... 514/258, 259, 269, 241, 514/256; 544/319, 298, 322, 326, 327, 283, 253, 287, 288, 293, 217, 180, 328, 334

[56] References Cited

U.S. PATENT DOCUMENTS 4,413,999 11/1983 Linder et al. ........................... 8/540

Primary Examiner—John M. Ford
Attorney, Agent, or Firm—Sprung Horn Kramer & Woods

[57] ABSTRACT

New substituted pyrimidylamide oximes of the general formula (I)

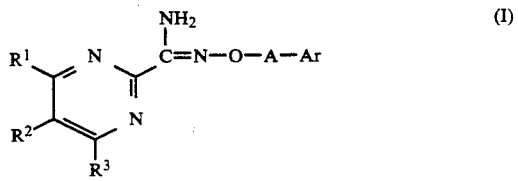

in which $R^1$, $R^2$, $R^3$, A and Ar have the meanings given in the description, new intermediates for their preparation, and their use for combating pests.

The new compounds of the formula (I) can be prepared by analogous processes, for example by reacting suitable pyrimidylamide oximes with suitable alkylating agents. The starting compounds which are also new, namely the pyrimidylamide oximes of the formula (II) in which —A—Ar represents hydrogen, can be prepared from suitable cynaopyrimidines with hydroxylamine or its acid adducts.

7 Claims, No Drawings

SUBSTITUTED PYRIMIDYLAMIDE OXIMES

The invention relates to new substituted pyrimidylamide oximes, to a process and new intermediates for their preparation and to their use as pesticides, in particular as fungicidesy.

Pyrimidine-2-amide oxime is already known from the literature (cf. Ann. Chim. (Paris) 5 (1960), 351–379—cited in Chem. Abstracts 56 (1962), 5961–5962). However, nothing has been disclosed as regards the biological properties of this compound.

Certain fungicidally active oximes such as, for example, α-(4-methylphenylsulphonyl)-O-(4-methyl-phenylsulphonylaminocarbonyl)-2,6-dichloro-benzaldoxime and α-(4-methylphenylsulphonyl)-O-(4-methyl-phenylaminocarbonyl)-2,6-dichlorobenzaldoxime (cf. EP-A 205,076), α-(4-chlorophenylsulphonyl)-O-cyclohexylaminocarbonyl-2,6-dichlorobenzaldoxime (cf. EP-A 281,901), α-(4-chloro-phenylsulphonyl)-O-ethoxycarbonyl-pyridine-3-aldoxime and α-(4-methyl-phenylsulphonyl)-O-ethoxycarbonyl-6-methylpyridine-2-aldoxime (cf. EP-A 236,897) as well as α-(4-methyl-phenylsulphonyl)-6-methyl-pyridine-2-aldoxime, α-(4-chloro-phenylsulphonyl)-pyridine-4-aldoxime and α-phenylsulphonyl-6-methylpyridine-2-aldoxime (cf. EP-A 236,919), are already known. However, the action of these compounds is not entirely satisfactory when low amounts are applied.

New substituted pyrimidylamide oximes of the general formula (I)

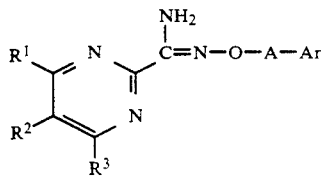

in which
R¹, R² and R³ are identical or different and represent hydrogen, halogen, alkyl, halogenoalkyl, alkoxyalkyl, alkoxy, halogenoalkoxy, alkoxyalkoxy, alkylthio, alkylamino or dialkylamino, it also being possible for two of these radicals R¹ and R² or R² and R³ together to represent alkanediyl,
A represents alkanediyl and
Ar represents in each case optionally substituted aryl or heteroaryl,
have now been found.

Furthermore, it has been found that the new compounds of the formula (I) are obtained when pyrimidylamide oximes of the general formula (II)

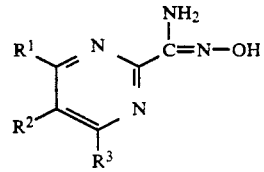

in which
R¹, R² and R³ are identical or different and represent hydrogen, halogen, alkyl, halogenoalkyl, alkoxyalkyl, alkoxy, halogenoalkoxy, alkoxyalkoxy, alkylthio, alkylamino or dialkylamino, it also being possible for two of these radicals R¹ and R² or R² and R³ together to represent alkanediyl, are reacted with alkylating agents of the general formula (III)

$$X\text{—}A\text{—}Ar \qquad (III)$$

in which
A represents alkanediyl,
Ar represents in each case optionally substituted aryl or heteroaryl and
X represents halogen,
if appropriate in the presence of an acid acceptor and if appropriate in the presence of a diluent.

The new substituted pyrimidylamide oximes of the general formula (I) show a powerful action as pesticides, in particular as fungicides, and, to a certain extent, also as insecticides.

Surprisingly, the new compounds of the formula (I) show a considerably more powerful action than the known compounds α-(4-methyl-phenylsulphonyl)-O-(4-methyl-phenylsulphonylaminocarbonyl)-2,6-dichloro-benzaldoxime and α-(4-methyl-phenylsulphonyl)-O-(4-methyl-phenylaminocarbonyl)-2,6-dichloro-benzaldoxime (cf. EP-A 205,076), α-(4-chloro-phenylsulphonyl)-O-cyclohexylaminocarbonyl-2,6-dichloro-benzaldoxime (cf. EP-A 281,901), α-(4-chloro-phenylsulphonyl)-O-ethoxycarbonyl-pyridine-3-aldoxime and α-(4-methyl-phenylsulphonyl)-O-ethoxycarbonyl-6-methyl-pyridine-2-aldoxime (cf. EP-A 236,897) as well as α-(4-methyl-phenylsulphonyl)-6-methyl-pyridine-2-aldoxime and α-phenylsulphonyl-6-methyl-pyridine-2-aldoxime (cf. EP-A 236,919).

Preferred substituents will be illustrated in the following text: alkyl in the general formulae, on its own or in compound radicals such as, for example, alkoxy, alkylthio or alkylamino, in each case represents straight-chain or branched alkyl, preferably having 1 to 6, in particular having 1 to 4, carbon atoms. The following may be mentioned by way of example: methyl, ethyl, n- and isopropyl, n-, iso-, sec- and tert-butyl.

Halogenoalkyl in the general formulae, on its own or in compound radicals such as, for example, halogenoalkoxy, in each case represents straight-chain or branched halogenoalkyl, preferably having 1 to 6 carbon atoms and 1 to 13 halogen atoms, preferably fluorine or chlorine atoms, in particular having 1 to 4 carbon atoms and 1 to 9 halogen atoms. The following may be mentioned by way of example: fluoromethyl, chloromethyl, difluoromethyl, dichloromethyl, trifluoromethyl, trichloromethyl, chlorofluoromethyl, chlorodifluoromethyl, fluorodichloromethyl, fluoroethyl, difluoroethyl, trifluoroethyl, tetrafluoroethyl, chloroethyl, dichloroethyl, trichloroethyl, chlorofluoroethyl, chlorodifluoroethyl, chlorotrifluoroethyl, fluoropropyl, chloropropyl, fluorobutyl and chlorobutyl.

Alkanediyl in the general formulae in each case represents straight-chain or branched alkanediyl, preferably having 1 to 5, in particular having 1 to 4, carbon atoms. The following may be mentioned by way of example: methane-1,1-diyl (methylene), ethane-1,1-diyl (ethylidene), ethane-1,2-diyl (dimethylene), propane-1,1-diyl (propylidene), propane-1,2-diyl, propane-1,3-diyl and butane-1,4-diyl.

Halogen in the general formulae represents fluorine, chlorine, bromine or iodine, preferably fluorine, chlorine or bromine, in particular fluorine or chlorine.

Aryl in the general formulae preferably represents phenyl or naphthyl, in particular phenyl.

Heteroaryl in the general formulae preferably represents five-membered or six-membered, optionally benzo-fused, aromatic heterocycles having up to 3 nitrogen atoms and/or, optionally, an oxygen or sulphur atom, in particular furyl, thienyl, pyrrolyl, pyrazolyl, imidazolyl, triazolyl, oxazolyl, benzoxazolyl, isoxazolyl, thiazolyl, benzthiazolyl, oxadiazolyl, thiadiazolyl, pyridyl, pyrimidyl and triazinyl.

The aryl substituents and heteroaryl substituents which are possible are preferably selected from the series comprising halogen, cyano, carboxyl, nitro, phenyl, in each case straight-chain or branched alkyl, alkoxy, alkylthio or alkoxycarbonyl preferably in each case having up to 4 carbon atoms, alkanediyl preferably having 3 or 4 carbon atoms, alkylenedioxy preferably having 1 or 2 carbon atoms, in each case straight-chain or branched halogenoalkyl, halogenoalkyloxy or halogenoalkylthio preferably having in each case up to 4 carbon atoms and preferably up to 9 halogen atoms, halogenoalkylenedioxy preferably having 1 or 2 carbon atoms and preferably up to 4 halogen atoms, or phenoxy which optionally contains the aryl substituents and heteroaryl substituents mentioned above. In particular, the aryl substituents and heteroaryl substituents which are possible are selected from the series comprising fluorine, chlorine, bromine, cyano, methyl, ethyl, methoxy, ethoxy, methylthio, ethylthio, methoxycarbonyl, ethoxycarbonyl, trifluoromethyl, trifluoromethoxy, trifluoromethylthio, methylenedioxy, ethylenedioxy,difluoromethylenedioxy,trifluoroethylenedioxy, tetrafluoroethylenedioxy,chlorotrifluoroethylenedioxy, or phenoxy which optionally contains the aryl substituents and heteroaryl substituents which have been mentioned above.

Formula (I) provides a general definition of the substituted pyrimidylamide oximes according to the invention. Preferred compounds of the formula (I) are those in which $R^1$ represents hydrogen, halogen, $C_1-C_4$-alkyl, $C_1-C_4$-halogenoalkyl, $C_1-C_2$-alkoxy-$C_1-C_2$-alkyl, $C_1-C_4$-alkoxy, $C_1-C_4$-halogenoalkoxy, $C_1-C_2$-alkoxy-$C_1-C_2$-alkoxy, $C_1-C_4$-alkylthio, $C_1-C_4$-alkylaminoor di-($C_1-C_2$-alkyl)-amino, $R^2$ represents hydrogen, halogen, $C_1-C_4$-alkyl, $C_1-C_4$-halogenoalkyl or $C_1-C_4$-alkoxy, or together with $R^1$ or $R^3$ represents trimethylene or tetramethylene, $R^3$ represents hydrogen, halogen, $C_1-C_4$-alkyl, $C_1-C_4$-halogenoalkyl, $C_1-C_4$-alkoxy or $C_1-C_4$-halogenoalkoxy, A represents $C_1-C_5$-alkanediyl and Ar represents in each case optionally substituted phenyl or naphthyl, or represents optionally substituted and/or optionally benzo-fused five-membered or six-membered heteroaryl having up to 3 nitrogen atoms and/or, optionally, an oxygen or sulphur atom, the substituents which are possible preferably being selected from the series comprising halogen, cyano, carboxyl, nitro, phenyl, in each case straight-chain or branched alkyl, alkoxy, alkylthio or alkoxycarbonyl, in each case having up to 4 carbon atoms, alkanediyl having 3 or 4 carbon atoms, alkylenedioxy having 1 or 2 carbon atoms, in each case straight-chain or branched halogenoalkyl, halogenoalkyloxy or halogenoalkylthio, in each case having up to 4 carbon atoms and up to 9 halogen atoms, halogenoalkylenedioxy having 1 or 2 carbon atoms and up to 4 halogen atoms, or phenoxy which optionally contains the substituents mentioned previously in the case of aryl and heteroaryl.

Particularly preferred compounds of the formula (I) are those in which $R^1$ represents hydrogen, fluorine, chlorine, bromine, methyl, ethyl, trifluoromethyl, chloromethyl, methoxymethyl, methoxy, ethoxy, difluoromethoxy, 2,2,2-trifluoroethoxy,2-methoxy-ethoxy,methylthio, methylamino, ethylamino or dimethylamino, $R^2$ represents hydrogen, fluorine, chlorine, bromine, methyl, trifluoromethyl or methoxy, $R^3$ represents hydrogen, fluorine, chlorine, bromine, methyl, ethyl, propyl, trifluoromethyl, chloromethyl, methoxy, ethoxy or difluoromethoxy, A represents methane-1,1-diyl (methylene), ethane-1,1-diyl (ethylidene) or ethane-1,2-diyl (dimethylene), and Ar represents in each case optionally substituted phenyl, naphthyl, furyl, thienyl, pyrrolyl, pyrazolyl, imidazolyl, triazolyl, oxazolyl, benzoxazolyl, isoxazolyl, thiazolyl, benzthiazolyl, oxadiazolyl, thiadiazolyl, pyridyl, pyrimidyl or triazinyl, the substituents which are possible being selected, in particular, from the series comprising fluorine, chlorine, bromine, cyano, phenyl, methyl, ethyl, methoxy, ethoxy, methylthio, ethylthio, methoxycarbonyl, ethoxycarbonyl, trifluoromethyl, trifluoromethoxy, trifluoromethylthio, methylenedioxy, ethylenedioxy, difluoromethylenedioxy, trifluoromethylenedioxy, tetrafluoroethylenedioxy, chlorotrifluoroethylenedioxy, or phenoxy which optionally contains the substituents previously mentioned in the case of the aryl and heteroaryl radicals.

The aryl and/or heteroaryl radicals can preferably be mono- to pentasubstituted, in particular mono- to tetrasubstituted and very particularly mono- to trisubstituted by identical or different substituents.

If, for example, 4,6-dimethyl-pyrimidine-2-carbamide oxime and 3,4-dichloro-benzyl chloride are used as starting materials, the course of the reaction in the preparation process according to the invention can be represented by the following equation:

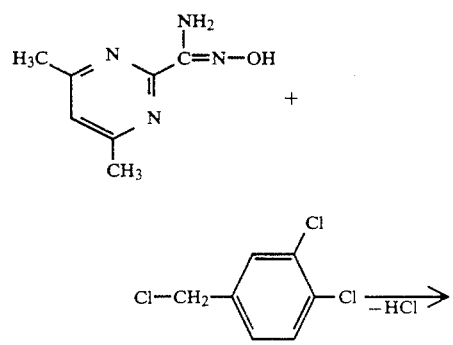

-continued

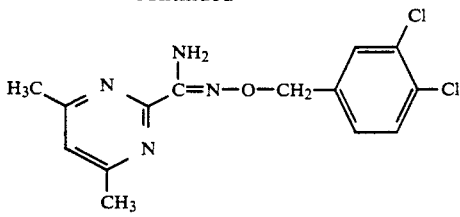

Formula (II) provides a general definition of the pyrimidylamide oximes to be used as starting materials in the process according to the invention for the preparation of compounds of the formula (I).

In formula (II), $R^1$, $R^2$ and $R^3$ preferably, or in particular, have those meanings which have already been mentioned above in connection with the description of the compounds of the formula (I) according to the invention as being preferred, or as particularly preferred for $R^1$, $R^2$ and $R^3$.

The following may be mentioned as examples of the starting materials of the formula (II):

Pyrimidine-2-carbamide oxime, 4-methyl-, 5-methyl-, 4,5-dimethyl-, 4,6-dimethyl-, 4,5,6-trimethyl-, 4-methoxy-, 5-methoxy-, 4-methoxy-6-methyl-, 4-methoxy-5-methyl-, 5-methoxy-4-methyl-, 4,6-dimethoxy-, 4-methoxy-6-ethyl-, 4-ethoxy-6-methyl-, 4-methoxy-6-trifluoromethyl-, 4,6-diethoxy- and bis-4,6-difluoromethoxypyrimidine-2-carbamide oxime.

With the exception of pyrimidine-2-carbamide oxime (pyrimidine-2-amide oxime, —(II), $R^1=R^2=R^3=H$—cf. Ann. Chim. (Paris) 5 (1960), 351-379), the starting materials of the formula (II) are new and part of the present invention.

The new pyrimidylamide oximes of the formula (II) are obtained when cyanopyrimidines of the general formula (IV)

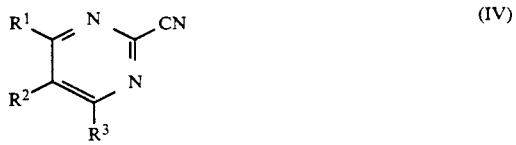

in which $R^1$, $R^2$ and $R^3$ have the abovementioned meaning, are reacted with hydroxylamine or its acid adducts such as, for example, hydroxylammonium chloride, if appropriate in the presence of an acid acceptor such as, for example, sodium carbonate, and if appropriate in the presence of diluents such as, for example, ethanol and water, at temperatures between 20° C. and 100° C.

In formula (IV), $R^1$, $R^2$ and $R^3$ preferably, or in particular, have those meanings which have already been mentioned above in connection with the description of the compounds of the formula (I) according to the invention as being preferred, or as particularly preferred, for $R^1$, $R^2$ and $R^3$.

The following may be mentioned as examples of the compounds of the formula (IV): 4,5-dimethyl-, 4,6-dimethyl-, 4,5,6-trimethyl-, 4-methoxy-, 5-methoxy-, 4-methoxy-6-methyl-, 4-methoxy-5-methyl-, 5-methoxy-4-methyl-, 4,6-dimethoxy-, 4-methoxy-6-ethyl-, 4-ethoxy-6-methyl-, 4-methoxy-6-trifluoromethyl-, 4,6-diethoxy- and bis-4,6-difluoromethoxypyrimidine-2-carbonitrile.

The cyanopyrimidines of the formula (IV) are known and/or can be prepared by processes known per se (cf. Beilstein E III/IV, Volume 25, 783-791; Monatshefte Chemie 87 (1956), 526-546; Chem. Pharm. Bull. 6 (1958), 633-638).

Formula (III) provides a general definition of the alkylating agents furthermore to be used as starting materials in the process according to the invention for the preparation of compounds of the formula (I).

In formula (III), A and Ar preferably, or in particular, have those meanings which have already been mentioned above in connection with the description of the compounds of the formula (I) according to the invention as being preferred, or as particularly preferred, for A and Ar; X represents fluorine, chlorine, bromine or iodine, preferably chlorine or bromine.

Examples of the starting materials of the formula (III) which may be mentioned are: benzyl chloride, 1-phenyl- and 2-phenyl-ethyl chloride, 2-fluoro-, 3-fluoro-, 4-fluoro-, 2,4-difluoro-, 2,6-difluoro- and 3,4-difluoro-benzyl chloride, 2-chloro-, 3-chloro-, 4-chloro-, 2,4-dichloro-, 2,6-dichloro- and 3,4-dichloro-benzyl chloride, 2-bromo-, 3-bromo- and 4-bromo-benzyl chloride, 4-cyano-benzyl chloride, 2-methyl-, 3-methyl-, 4-methyl-, 2,3-dimethyl-, 2,4-dimethyl-, 2,6-dimethyl-, 2,5-dimethyl-, 3,4-dimethyl- and 2,4,6-trimethyl-benzyl chloride, 2-methoxy-, 3-methoxy-, 4-methoxy- and 3,4-dimethoxy-benzyl chloride, 3-methoxycarbonyl- and 4-methoxycarbonyl-benzyl chloride, 2-trifluoromethyl-, 3-trifluoromethyl- and 4-trifluoromethylbenzyl chloride, 4-trifluoromethoxy- and 4-trifluoromethylthio-benzyl chloride, 3,4-methylenedioxybenzyl chloride, 4-phenoxy- and 3-phenoxy-benzyl chloride, 1-chloromethyl- and 2-chloromethyl-naphthalene, and also the corresponding bromoalkyl compounds.

The starting materials of the formula (III) are known chemicals for synthesis.

The process according to the invention for the preparation of the new compounds of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoric triamide.

Acid acceptors which can be employed in the process according to the invention are all acid-binding agents which can customarily be used for reactions of this type. The following are preferably suitable: alkali metal hydrides and alkaline earth metal hydrides such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate, potassium carbonate, sodium hydrogen carbonate and potassium hydrogen carbonate, and also calcium carbonate, alkali metal acetates such as sodium acetate and potassium acetate, alkali metal alcoholates such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tertbutylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]octane (DABCO).

When carrying out the process according to the invention, the reaction temperatures can be varied within a substantial range. In general, the process is carried out at temperatures between 0° C. and 150° C., preferably at temperatures between 20° C. and 120° C.

The process according to the invention is generally carried out under atmospheric pressure. However, it is also possible to carry out the process under increased or reduced pressure.

For carrying out the process according to the invention, the starting materials required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the particular temperature required. Working-up in the process according to the invention is carried out in each case by customary methods.

The active compounds according to the invention exhibit a powerful biological action and can be employed in practice for combating pests. The active compounds can preferably be employed for use in plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In particular, the compounds of the formula (I) according to the invention show a powerful protective action against Venturia species such as, for example, against Venturia inaequalis on apples, aqainst Cochliobolus species such as, for example, *Cochliobolus sativus* on barley, and against Pyrenophora species such as, for example, against *Pyrenophora teres* on barley. A powerful action is also to be observed against *Pyricularia oryzae* on rice.

To a certain extent, other fungal plant pests such as, for example, *Erysiphe graminis*, Fusarium nivale and Septoria nodorum on cereals, but also animal pests, such as insects and nematodes, can also be combated with the compounds of the formula (I).

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in a customary manner, for example by watering, spraying, atomizing, scattering, dusting, foaming, brushing on etc. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

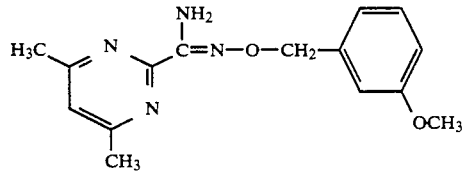

A mixture of 2.5 g (15 mmol) of 4,6-dimethyl-pyrimidine-2-carbamide oxime, 2.82 g (15 mmol) of 3-methoxy-benzyl chloride, 2.07 g (15 mmol) of potassium carbonate and 50 ml of acetonitrile is refluxed gently for 14 hours, with stirring. The mixture is subsequently cooled to room temperature and filtered, and the filtrate is concentrated under a water pump vacuum. The residue is brought to crystallisation by stirring with petroleum ether, and the crystalline product is isolated by filtration with suction.

3.7 g (86 % of theory) of O-(3-methoxy-benzyl)-4,6-dimethyl-pyrimidine-2-carbamide oxime of melting point 83° C. are obtained.

Other examples of the compounds of the formula (I) which can be prepared analogously to Example 1 and following the general description of the preparation process according to the invention are those listed in Table 1 below.

TABLE 1
Examples of the compounds of the formula (I)
| Ex. No. | $R^1$ | $R^2$ | $R^3$ | A | Ar | Physical data |
|---|---|---|---|---|---|---|
| 2 | H | OCH$_3$ | H | CH$_2$ | 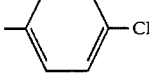 | m.p.: 138° C. |
| 3 | H | OCH$_3$ | H | CH$_2$ | 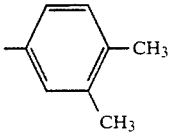 | m.p.: 121° C. |
| 4 | CH$_3$ | H | OCH$_3$ | CH$_2$ | 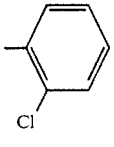 | (oil) |
| 5 | CH$_3$ | CH$_3$ | CH$_3$ | CH$_2$ | 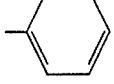 | m.p.: 152° C. |
| 6 | CH$_3$ | CH$_3$ | CH$_3$ | CH(CH$_3$) | 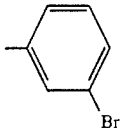 | m.p.: 115° C. |
| 7 | CH$_3$ | CH$_3$ | CH$_3$ | CH$_2$ | 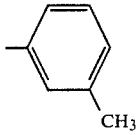 | m.p.: 93° C. |
| 8 | CH$_3$ | CH$_3$ | CH$_3$ | CH$_2$ | 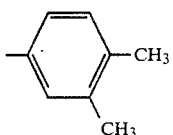 | m.p.: 94° C. |
| 9 | CH$_3$ | CH$_3$ | CH$_3$ | CH$_2$ | 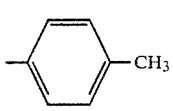 | m.p.: 103° C. |
| 10 | CH$_3$ | CH$_3$ | CH$_3$ | CH$_2$ | —C$_6$H$_4$—CH$_3$ | m.p.: 143° C. |

TABLE 1-continued
Examples of the compounds of the formula (I)
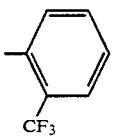
| Ex. No. | R¹ | R² | R³ | A | Ar | Physical data |
|---|---|---|---|---|---|---|
| 11 | $CH_3$ | $CH_3$ | $CH_3$ | $CH_2$ | 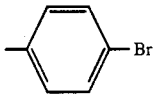 | m.p.: 111° C. |
| 12 | $CH_3$ | H | $OCH_3$ | $CH_2$ | 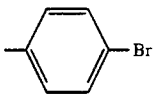 | m.p.: 114° C. |
| 13 | $OCH_3$ | H | $OCH_3$ | $CH_2$ |  | (oil) |
| 14 | $CH_3$ | $CH_3$ | $CH_3$ | $CH_2CH_2$ | 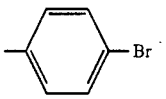 | m.p.: 105° C. |
| 15 | $CH_3$ | H | $CH_3$ | $CH_2$ |  | m.p.: 112° C. |
| 16 | $CH_3$ | H | $CH_3$ | $CH_2$ | 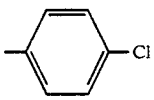 | δ = 5,30*) |
| 17 | $CH_3$ | H | $CH_3$ | $CH_2$ | 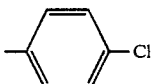 | (oil) |
| 18 | $CH_3$ | H | $CH_3$ | $CH_2$ | 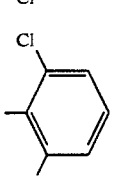 | m.p.: 121° C. |
| 19 | $CH_3$ | H | $CH_3$ | $CH_2$ | 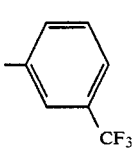 | (oil) |
| 20 | $CH_3$ | H | $CH_3$ | $CH_2$ |  | δ = 5,35*) |

TABLE 1-continued

Examples of the compounds of the formula (I)

$$R^1 \underset{R^2}{\overset{N}{\underset{R^3}{\bigg|}}} \overset{NH_2}{\underset{N}{\bigg|}} C=N-O-A-Ar \quad (I)$$

| Ex. No. | $R^1$ | $R^2$ | $R^3$ | A | Ar | Physical data |
|---|---|---|---|---|---|---|
| 21 | $CH_3$ | H | $CH_3$ | $CH_2$ | 4-$OCH_3$-phenyl | δ = 5,29*) |
| 22 | $CH_3$ | H | $CH_3$ | $CH_2$ | 2-F-phenyl | m.p.: 122° C. |
| 23 | $CH_3$ | H | $CH_3$ | $CH_2$ | 4-F-phenyl | m.p.: 59° C. |
| 24 | $CH_3$ | H | $CH_3$ | $CH_2$ | 4-$CH_3$-phenyl | δ = 5,26*) |
| 25 | $CH_3$ | H | $CH_3$ | $CH_2$ | 4-(phenoxy)-3-F-phenyl | δ = 5,21*) |
| 26 | $CH_3$ | H | $CH_3$ | $CH_2$ | 4-(4-$CF_3$-phenoxy)-phenyl | δ = 5,30*) |
| 27 | $CH_3$ | H | $CH_3$ | $CH_2$ | 2-Cl-phenyl | m.p.: 101° C. |
| 28 | $CH_3$ | H | $CH_3$ | $CH_2$ | 3-Cl-phenyl | m.p.: 77° C. |
| 29 | $CH_3$ | H | $CH_3$ | $CH_2$ | 4-$OCF_3$-phenyl | δ = 5,29*) |
| 30 | $CH_3$ | H | $CH_3$ | $CH_2$ | 4-$SCF_3$-phenyl | δ = 5,34*) |

TABLE 1-continued
Examples of the compounds of the formula (I)
$$\text{(I)}$$
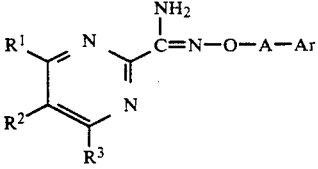
| Ex. No. | R¹ | R² | R³ | A | Ar | Physical data |
|---|---|---|---|---|---|---|
| 31 | CH₃ | H | CH₃ | CH₂ | 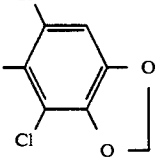 | m.p.: 127° C. |
| 32 | CH₃ | H | OCH₃ | CH₂ | 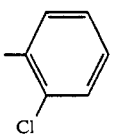 | δ = 5,28*) |
| 33 | CH₃ | H | OCH₃ | CH₂ | 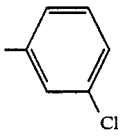 | δ = 5,40*) |
| 34 | CH₃ | H | OCH₃ | CH₂ | 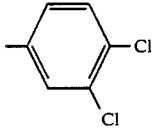 | δ = 5,24*) |
| 35 | CH₃ | H | CH₃ | CH₂ | 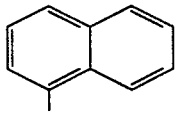 | m.p.: 81° C. |
| 36 | CH₃ | H | CH₃ | CH₂ | 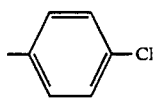 | m.p.: 85° C. |
| 37 | CH₃ | H | OCH₃ | CH₂ | 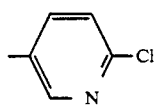 | m.p.: 87° C. |
| 38 | CH₃ | H | CH₃ | CH₂ | 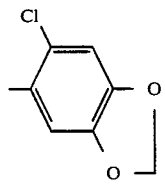 | (oil) |
| 39 | CH₃ | H | CH₃ | CH₂ |  | (oil) |

TABLE 1-continued

Examples of the compounds of the formula (I)

$$R^1\text{-pyrimidine ring with } R^2, R^3 \text{ substituents, } C(NH_2)=N-O-A-Ar$$ (I)

| Ex. No. | R¹ | R² | R³ | A | Ar | Physical data |
|---|---|---|---|---|---|---|
| 40 | CH₃ | H | H | CH₂ | phenyl | (oil) |
| 41 | CH₃ | H | H | CH₂ | 4-Cl-phenyl | (oil) |
| 42 | CH₃ | H | H | CH₂ | 3-Cl-phenyl | m.p.: 110° C. |
| 43 | CH₃ | H | H | CH₂ | 2-Cl-phenyl | m.p.: 135° C. |
| 44 | CH₃ | H | CH₃ | CH₂ | 2,6-F₂-phenyl | m.p.: 128° C. |
| 45 | CH₃ | H | CH₃ | CH₂CH₂ | phenyl | (oil) |
| 46 | OCH₃ | H | C₃H₇ | CH₂ | 3-Cl-phenyl | δ = 5,23*) |
| 47 | CH₃ | H | CH₃ | CH₂ | 3,4-(OCH₃)₂-phenyl | (oil) |
| 48 | CH₃ | H | CH₃ | CH₂ | 3,4-methylenedioxy-phenyl | (oil) |

TABLE 1-continued

Examples of the compounds of the formula (I)

$$\underset{R^3}{\underset{R^2}{R^1}}\overset{N}{\underset{N}{\bigvee}}\overset{NH_2}{\underset{C=N-O-A-Ar}{|}}\quad (I)$$

| Ex. No. | R¹ | R² | R³ | A | Ar | Physical data |
|---|---|---|---|---|---|---|
| 49 | CH₃ | H | H | CH₂ | 3,4-dimethoxyphenyl | (oil) |
| 50 | CH₃ | H | H | CH₂ | 3,4-methylenedioxyphenyl | (oil) |
| 51 | CH₃ | H | CH₃ | CH₂ | 3-(COOCH₃)phenyl | (oil) |
| 52 | CH₃ | H | OCH₃ | CH₂ | 3-(COOCH₃)phenyl | (oil) |
| 53 | OCH₃ | H | H | CH₂ | 3-Cl-phenyl | (oil) |
| 54 | OCH₃ | —(CH₂)₃— | | CH₂ | 4-Cl-phenyl | δ = 5,25*) |
| 55 | CH₃ | H | CH₃ | CH₂ | 2-naphthyl | δ = 5,46*) |
| 56 | CH₃ | H | OCH₃ | CH₂ | 2-naphthyl | δ = 5,44*) |
| 57 | CH₃ | CH₃ | CH₃ | CH₂ | 4-Cl-phenyl | m.p.: 101° C. |

TABLE 1-continued
Examples of the compounds of the formula (I)
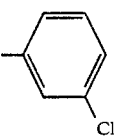
| Ex. No. | R¹ | R² | R³ | A | Ar | Physical data |
|---|---|---|---|---|---|---|
| 58 | $CH_3$ | $CH_3$ | $CH_3$ | $CH_2$ | 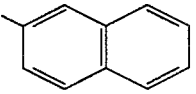 | m.p.: 89° C. |
| 59 | $CH_3$ | $CH_3$ | $CH_3$ | $CH_2$ | 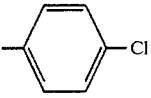 | m.p.: 95° C. |
| 60 | $OCH_3$ | H | $OCH_3$ | $CH_2$ | 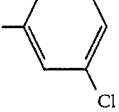 | (oil) |
| 61 | $OCH_3$ | H | $OCH_3$ | $CH_2$ | 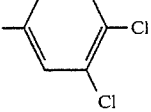 | (oil) |
| 62 | $OCH_3$ | H | $OCH_3$ | $CH_2$ | 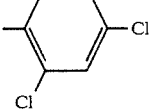 | (oil) |
| 63 | $OCH_3$ | H | $OCH_3$ | $CH_2$ | 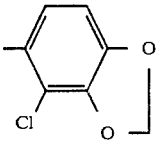 | (oil) |
| 64 | $OCH_3$ | H | $OCH_3$ | $CH_2$ | 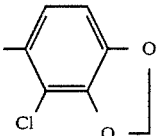 | (oil) |
| 65 | $CH_3$ | H | $OCH_3$ | $CH_2$ | 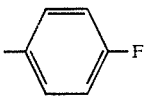 | (oil) |
| 66 | $CH_3$ | H | $OCH_3$ | $CH_2$ |  | (oil) |

TABLE 1-continued
Examples of the compounds of the formula (I)
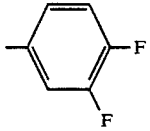
| Ex. No. | R¹ | R² | R³ | A | Ar | Physical data |
|---|---|---|---|---|---|---|
| 67 | CH₃ | H | OCH₃ | CH₂ | 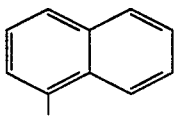 3,4-F₂-C₆H₃ | (oil) |
| 68 | CH₃ | H | OCH₃ | CH₂ | 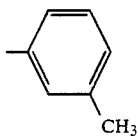 1-naphthyl | m.p.: 89° C. |
| 69 | CH₃ | H | OCH₃ | CH₂ | 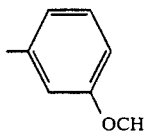 3-CH₃-C₆H₄ | δ = 5,25*) |
| 70 | CH₃ | H | OCH₃ | CH₂ | 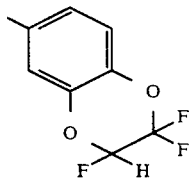 3-OCH₃-C₆H₄ | (oil) |
| 71 | CH₃ | H | OCH₃ | CH₂ | 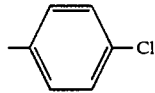 | (oil) |
| 72 | OC₂H₅ | H | OC₂H₅ | CH₂ | 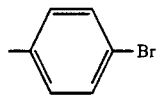 4-Cl-C₆H₄ | (oil) |
| 73 | OC₂H₅ | H | OC₂H₅ | CH₂ | 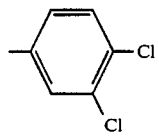 4-Br-C₆H₄ | (oil) |
| 74 | CH₃ | H | H | CH₂ | 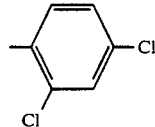 3,4-Cl₂-C₆H₃ | (oil) |
| 75 | CH₃ | H | H | CH₂ | 2,4-Cl₂-C₆H₃ | (oil) |

TABLE 1-continued

Examples of the compounds of the formula (I)

$$R^1, R^2, R^3, A, Ar \text{ substituents on pyrimidine oxime ether (I)}$$

| Ex. No. | $R^1$ | $R^2$ | $R^3$ | A | Ar | Physical data |
|---|---|---|---|---|---|---|
| 76 | CH$_3$ | H | H | CH$_2$ | 2-F-C$_6$H$_4$ | (oil) |
| 77 | CH$_3$ | H | OCH$_3$ | CH$_2$ | 3,4-Cl$_2$-C$_6$H$_3$ | δ = 5,20*) |
| 78 | CH$_3$ | H | OCH$_3$ | CH$_2$ | 2,4-Cl$_2$-C$_6$H$_3$ | m.p.: 127° C. |
| 79 | CH$_3$ | H | H | CH$_2$ | 4-CH$_3$-C$_6$H$_4$ | (oil) |
| 80 | CH$_3$ | H | H | CH$_2$ | 3-OCH$_3$-C$_6$H$_4$ | (oil) |
| 81 | CH$_3$ | H | H | CH$_2$ | 3-F-C$_6$H$_4$ | (oil) |
| 82 | CH$_3$ | H | H | CH$_2$ | 2,4-F$_2$-C$_6$H$_3$ | (oil) |
| 83 | CH$_3$ | H | OCH$_3$ | CH$_2$ | 2-F-C$_6$H$_4$ | m.p.: 98° C. |
| 84 | CH$_3$ | H | OCH$_3$ | CH$_2$ | 4-CH$_3$-C$_6$H$_4$ | δ = 5,16*) |

TABLE 1-continued

Examples of the compounds of the formula (I)

$$\begin{array}{c} R^1 \\ \diagdown \\ R^2 \diagup \end{array} \begin{array}{c} N \\ \diagdown \\ \diagup \\ N \\ | \\ R^3 \end{array} \begin{array}{c} NH_2 \\ | \\ C=N-O-A-Ar \end{array} \quad (I)$$

| Ex. No. | $R^1$ | $R^2$ | $R^3$ | A | Ar | Physical data |
|---|---|---|---|---|---|---|
| 85 | $CH_3$ | H | H | $CH_2$ | 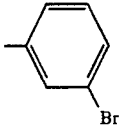 | (oil) |
| 86 | $CH_3$ | H | H | $CH_2$ | 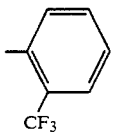 | (oil) |
| 87 | $CH_3$ | H | $CH_3$ | $CH_2$ | 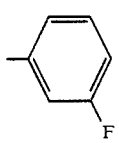 | m.p.: 69° C. |
| 88 | $CH_3$ | H | $CH_3$ | $CH_2$ | 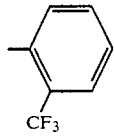 | m.p.: 81° C. |
| 89 | $CH_3$ | H | $OCH_3$ | $CH_2$ | 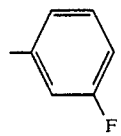 | δ = 5,27*) |
| 90 | $CH_3$ | H | $OCH_3$ | $CH_2$ | 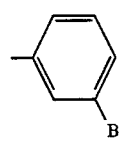 | δ = 5,23*) |
| 91 | $CH_3$ | H | $CH_3$ | $CH_2$ | 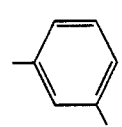 | (oil) |
| 92 | $CH_3$ | H | $CH_3$ | $CH_2$ | 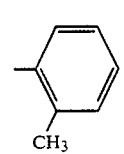 | m.p.: 143° C. |

TABLE 1-continued
Examples of the compounds of the formula (I)
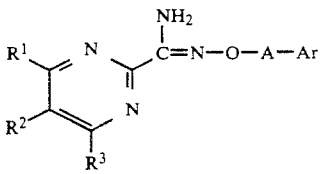
| Ex. No. | R¹ | R² | R³ | A | Ar | Physical data |
|---|---|---|---|---|---|---|
| 93 | CH₃ | H | CH₃ | CH₂ | 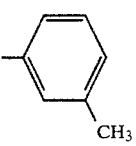 | (oil) |
| 94 | CH₃ | H | OCH₃ | CH₂ | 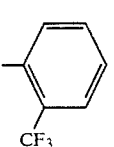 | (oil) |
| 95 | CH₃ | H | CH₃ | CH–CH₃ |  | (oil) |
| 96 | OCH₃ | —(CH₂)₃— | | CH₂ | 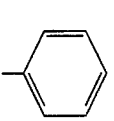 | (oil) |
| 97 | H | CH₃ | H | CH₂ | 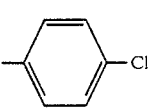 | (oil) |
| 98 | CH₃ | H | OCH₃ | CH₂ | 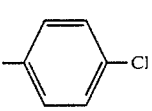 | (oil) |
| 99 | N(CH₃)₂ | H | OCH₃ | CH₂ | 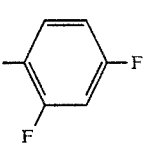 | (oil) |
| 100 | CH₃ | H | CH₃ | CH₂ | 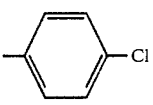 | m.p.: 76° C. |
| 101 | CH₃ | H | CH₃ | CH₂ | 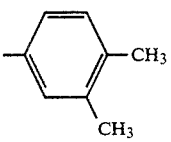 | (oil) |

TABLE 1-continued

Examples of the compounds of the formula (I)

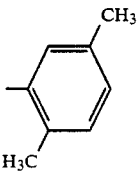

| Ex. No. | R¹ | R² | R³ | A | Ar | Physical data |
|---|---|---|---|---|---|---|
| 102 | CH₃ | H | CH₃ | CH₂ | 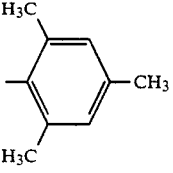 2,5-dimethylphenyl | m.p.: 128° C. |
| 103 | CH₃ | H | CH₃ | CH₂ | 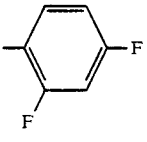 2,4,6-trimethylphenyl | (oil) |
| 104 | CH₃ | H | CH₃ | CH₂ | 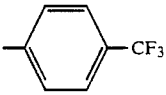 2,4-difluorophenyl | (oil) |
| 105 | CH₃ | H | CH₃ | CH₂ | 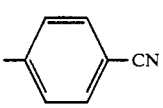 4-CF₃-phenyl | m.p.: 123° C. |
| 106 | CH₃ | H | CH₃ | CH₂ |  4-CN-phenyl | (oil) |
| 107 | CH₃ | H | CH₃ | CH₂ |  3,4-difluorophenyl | (oil) |
| 108 | OCH₃ | H | C₃H₇ | CH₂ |  4-Cl-phenyl | (oil) |
| 109 | OCH₃ | H | H | CH₂ | 4-Cl-phenyl | (oil) |
| 110 | OCH₃ | H | CH₃ | CH₂ | 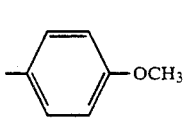 4-OCH₃-phenyl | m.p.: 96° C. |
| 111 | CH₃ | CH₃ | CH₃ | CH₂ | 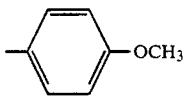 4-OCH₃-phenyl | m.p.: 135° C. |

TABLE 1-continued

Examples of the compounds of the formula (I)

$$R^1-C(=N-)-C(NH_2)=N-O-A-Ar \quad (I)$$

(structure with $R^1$, $R^2$, $R^3$ on pyrimidine-type ring with $NH_2$, $C=N-O-A-Ar$ substituent)

| Ex. No. | $R^1$ | $R^2$ | $R^3$ | A | Ar | Physical data |
|---|---|---|---|---|---|---|
| 112 | CH$_3$ | CH$_3$ | CH$_3$ | CH$_2$ | 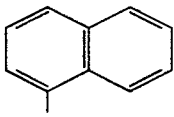 | (oil) |
| 113 | CH$_3$ | CH$_3$ | CH$_3$ | CH$_2$ | 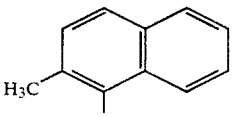 | m.p.: 139° C. |
| 114 | CH$_3$ | H | CH$_3$ | CH$_2$ | 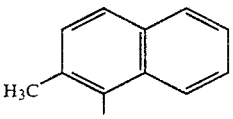 | m.p.: 151° C. |
| 115 | OCH$_3$ | H | CH$_3$ | CH$_2$ | 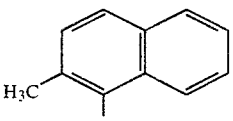 | m.p.: 96° C. |
| 116 | CH$_3$ | H | CH$_3$ | CH$_2$ | 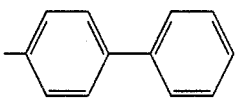 | (oil) |
| 117 | CH$_3$ | CH$_3$ | CH$_3$ | CH$_2$ | 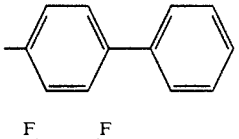 | m.p.: 121° C. |
| 118 | CH$_3$ | CH$_3$ | CH$_3$ | CH$_2$ | 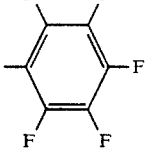 | m.p.: 131° C. |
| 119 | CH$_3$ | H | CH$_3$ | CH$_2$ | 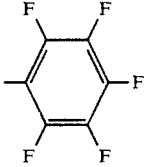 | m.p.: 101° C. |
| 120 | CH$_3$ | H | CH$_3$ | CH$_2$ | 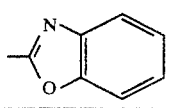 | m.p.: 132° C. |

*)$^1$H-NMR: δ values (ppm) for A=CH$_2$ (in CDCl$_3$)

STARTING MATERIALS OF THE FORMULA (II)

Example (II-1)

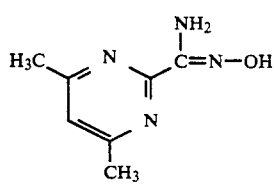

6.95 g (0.1 mol) of hydroxylamine hydrochloride are dissolved in 100 ml of ethanol. A solution of 10.6 g (0.1 mol) of sodium carbonate in 20 ml of water is then added, followed by 13.3 g (0.1 mol) of 4,6-dimethyl-pyrimidine-2-carbonitrile. The solution is refluxed for 14 hours, cooled and concentrated. The residue is taken up in 200 ml of methylene chloride, the methylene chloride solution is washed with a little water, dried over sodium sulphate, filtered and concentrated.

10.5 g (63 % of theory) of 4,6-dimethyl-pyrimidine-2-carbamide oxime are obtained as a crystalline residue of melting point 209° C.

Other examples of the compounds of the formula (II) which can be prepared analogously to Example (II-1) are those listed in Table 2 below.

TABLE 2

Examples of the compounds of the formula (II)

(II)

$$R^1 \quad N \quad \overset{NH_2}{\underset{N}{C=N-OH}}$$

$$R^2 \quad \underset{R^3}{\quad} N$$

| Ex. No. | R¹    | R²    | R³    | Physical data |
|---------|-------|-------|-------|---------------|
| II-2    | CH₃   | H     | H     | m.p.: 212° C. |
| II-3    | OC₂H₅ | H     | OC₂H₅ |               |
| II-4    | CH₃   | CH₃   | CH₃   | m.p.: 260° C. |
| II-5    | OCH₃  | H     | C₃H₇  |               |
| II-6    | OCH₃  | H     | H     |               |
| II-7    | OCH₃  | —(CH₂)₃— |    |               |
| II-8    | H     | OCH₃  | H     | m.p.: 205° C. |
| II-9    | CH₃   | H     | OCH₃  | m.p.: 184° C. |

USE EXAMPLES

In the use examples which follow, the compounds listed below are employed as comparison substances:

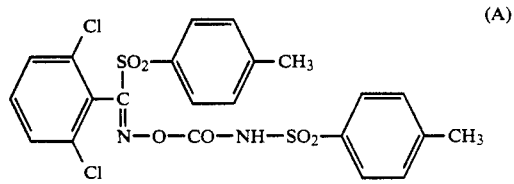

(A)

α-(4-methyl-phenylsulphonyl)-O-(4-methyl-phenylsulphonylaminocarbonyl)-2,6-dichloro-benzaldoxime (disclosed in EP-A 205,076, Example 1);

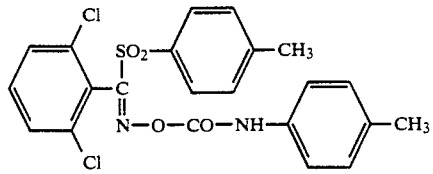

(B)

α-(4-methyl-phenylsulphonyl)-O-(4-methyl-phenylaminocarbonyl)-2,6-dichloro-benzaldoxime (disclosed in EP-A 205,076, Example 16);

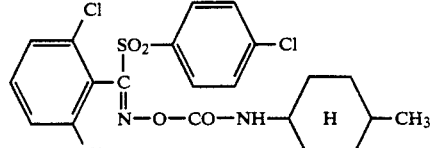

(C)

α-(4-chloro-phenylsulphonyl)-O-cyclohexylaminocarbonyl-2,6-dichloro-benzaldoxime (disclosed in EP-A 281,909, Example 60);

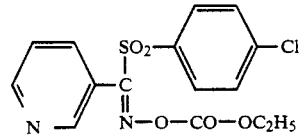

(D)

α-(4-chloro-phenylsulphonyl)-O-ethoxycarbonyl-pyridine-3-aldoxime (disclosed in EP-A 236,897, Example 5);

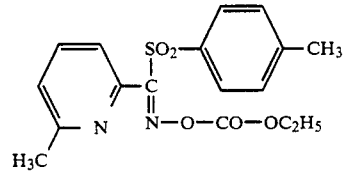

(E)

α-(4-methyl-phenylsulphonyl)-O-ethoxycarbonyl-6-methylpyridine-2-aldoxime (disclosed in EP-A 236,897, Example 10);

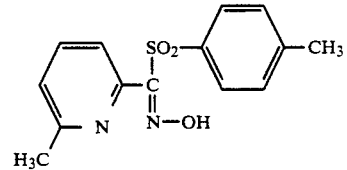

(F)

α-(4-methyl-phenylsulphonyl)-6-methyl-pyridine-2-aldoxime (disclosed in EP-A 236,919, Example 10);

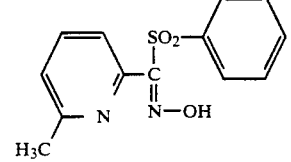

(G)

α-phenylsulphonyl-6-methyl-pyridine-2-aldoxime (disclosed in EP-A 236,919, Example 11);

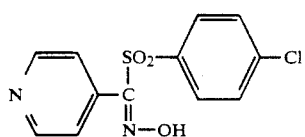

α-(4-chloro-phenylsulphonyl)-pyridine-4-aldoxime (disclosed in EP-A 236,919, Example 3).

Example A

Pyricularia Test (Rice)/Protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. When the spray coating has dried off, the plants are inoculated with an aqueous spore suspension of *Pyricularia oryzae*. The plants are then placed in a greenhouse at 25° C. and a relative atmospheric humidity of 100%.

The extent of disease is evaluated 4 days after the inoculation.

In this test, a clearly superior activity compared with the prior art is shown, for example, by the compounds of the following Preparation Examples: 12, 22, 28, 29, 30, 32, 54, 57, 58, 59 and 69.

Example B

Venturia Test (Apple)/Protective

Solvent 4 7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following Preparation Examples: 12, 15, 18, 20, 21, 22, 23, 24, 25, 26, 27, 28, 29, 33, 34, 35, 36, 37, 42, 43, 46, 55, 69, 77, 83, 87, 90, 91 and 105.

Example C

Cochliobolus sativus Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following Preparation Examples: 12, 16, 31, 35, 36, 44, 55, 68, 77, 83, 84, 88 and 89.

Example D

*Pyrenophora teres* Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried off, the plants are sprayed with a conidia suspension of *Pyrenophora teres*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following Preparation Examples: 1, 12, 15, 18, 20, 21, 22, 23, 24, 27, 28, 32, 33, 34, 37, 56, 68, 77, 88, 90 and 92.

We claim:

1. A substituted pyrimidylamide oxime of the formula (I)

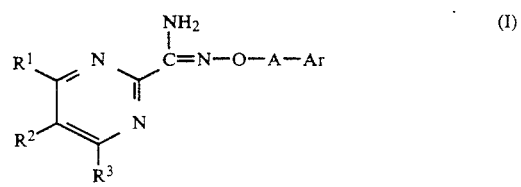

wherein $R^1$ represents hydrogen, halogen, $C_1-C_4$-alkyl, $C_1-C_4$-halogenoalkyl, $C_1-C_2$-alkoxy-$C_1-C_2$-alkyl, $C_1-C_4$-alkoxy, $C_1-C_4$-halogenoalkoxy, $C_1-C_2$-alkoxy-$C_1-C_2$-alkoxy, $C_1-C_4$-alkylthio, $C_1-C_4$-alkylamino or di-($C_1-C_2$-alkyl)-amino, $R^2$ represents hydrogen, halogen, $C_1-C_4$-alkyl, $C_1-C_4$-halogenoalkyl or $C_1-C_4$-alkoxy, or together with $R^1$ or $R^3$ represents trimethylene or tetramethylene, $R^3$ represents hydrogen, halogen, $C_1-C_4$-alkyl, $C_1-C_4$-halogenoalkyl, $C_1-C_4$-alkoxy or $C_1-C_4$-halogenoalkoxy, A represents $C_1-C_5$-alkanediyl and Ar represents optionally substituted phenyl or naphthyl, or represents furyl, thienyl, pyrrolyl, pyrazol imidazolyl, triazolyl, oxazolyl, benzoxazolyl, isoxazolyl, thiazolyl, benzthiazolyl, oxadiazolyl, thiadiazolyl, pyridyl, pyrimidyl or triazinyl, the substituents being selected from the group consisting of halogen, cyano, carboxyl, nitro, phenyl, straight-chain or branched alkyl, alkoxy, alkylthio or alkoxycarbonyl, in each case having up to 4 carbon atoms, alkanediyl having 3 or 4 carbon atoms, alkylenedioxy having 1 or 2 carbon atoms, straight-chain or branched halogenoalkyl, halogenoalkyloxy or halogenoalkylthio, in each case having up to 4 carbon atoms and up to 9 halogen atoms, halogenoalkylenedioxy having 1 or 2 carbon atoms and up to 4 halogen atoms, or phenoxy which optionally contains the substituents listed previously.

2. A substituted pyrimidylamide oxime according to claim 1, of the formula (I) wherein $R^1$ represents hydrogen, fluorine, chlorine, bromine, methyl, ethyl, trifluoromethyl chloromethyl, methoxymethyl, methoxy, ethoxy, difluoromethoxy, 2,2,2-trifluoroethoxy, 2-methoxy-ethoxy, methylthio, methylamino, ethylamino or dimethylamino, $R^2$ represents hydrogen, fluorine, chlorine, bromine, methyl, trifluoromethyl or methoxy, $R^3$ represents hydrogen, fluorine, chlorine, bromine, methyl, ethyl, propyl, trifluoromethyl, chloromethyl, methoxy, ethoxy or difluoromethoxy, A represents methane-1,1-diyl (methylene), ethane-1,1-diyl (ethylidene) or ethane-1,2-diyl (dimethylene), and Ar represents a member selected from the group consisting of optionally substituted phenyl, naphthyl, furyl, thienyl, pyrrolyl, pyrazolyl, imidazolyl, triazoyl, oxazolyl, benzoxazolyl, isoxazolyl, thiazolyl, benzthiazolyl, oxadiazolyl, thiadiazolyl, pyridyl, pyrimidyl and triazinyl, the substituents when present being selected from the group consisting of fluorine, chlorine, bromine, cyano, phenyl, methyl, ethyl, methoxy, ethoxy, methoxy, ethoxy, methylthio, ethylthio, methoxycarbonyl, ethoxycarbonyl, trifluoromethyl, trifluoromethoxy, trifluoromethylthio, methylenedioxy, ethylenedioxy, difluoromethylenedioxy, trifluoromethylenedioxy, tetrafluoroethylenedioxy, chlorotrifluoroethylenedioxy, and phenoxy which optionally contains the substituents previously listed.

3. A compound according to claim 1, wherein such compound is O-(naphthyl-1-methyl)-4,6-dimethylpyrimidine-2-carbamide oxime of the formula

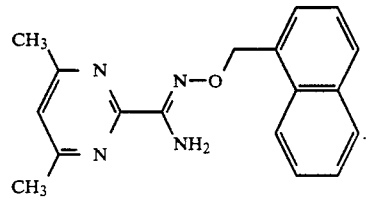

4. A compound according to claim 1, wherein such compound is O-(naphthyl-2-methyl)-4,5,6-trimethylpyrimidine-2-carbamide oxime of the formula

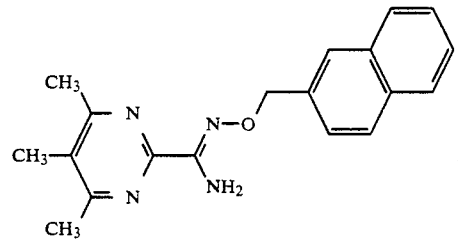

5. A fungicidal composition comprising a fungicidally effective amount of a compound according to claim 1 and a diluent.

6. A method of combating fungi which comprises applying to such fungi or to a fungus habitat a fungicidally effective amount of a compound according to claim 1.

7. A method according to claim 6, wherein such compound is O-(naphthyl-1-methyl)-4,6-dimethylpyrimidine-2-carbamide oxime or O-(naphthyl-2-methyl)-4,5,6-trimethylpyrimidine-2-carbamide oxime.

* * * * *